(12) United States Patent
Matsubara

(10) Patent No.: US 10,344,255 B2
(45) Date of Patent: Jul. 9, 2019

(54) CELL CULTURE OBSERVATION DEVICE AND METHOD TO DETERMINE A CONTENT OPERATION

(71) Applicant: FUJIFILM Corporation, Tokyo (JP)

(72) Inventor: Kenta Matsubara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 53 days.

(21) Appl. No.: 15/439,318

(22) Filed: Feb. 22, 2017

(65) Prior Publication Data

US 2017/0158998 A1 Jun. 8, 2017

Related U.S. Application Data

(63) Continuation of application No. PCT/JP2015/076554, filed on Sep. 17, 2015.

(30) Foreign Application Priority Data

Sep. 30, 2014 (JP) .................................. 2014-200942

(51) Int. Cl.
  *C12M 1/00* (2006.01)
  *C12M 1/34* (2006.01)
  *C12M 1/36* (2006.01)

(52) U.S. Cl.
  CPC ............ *C12M 23/34* (2013.01); *C12M 23/50* (2013.01); *C12M 29/00* (2013.01); *C12M 31/00* (2013.01); *C12M 41/36* (2013.01); *C12M 41/48* (2013.01)

(58) Field of Classification Search
  None
  See application file for complete search history.

(56) References Cited

U.S. PATENT DOCUMENTS

2006/0128005 A1   6/2006  Hasegawa et al.
2013/0196872 A1*  8/2013  Low ................. G01N 33/54353
                                                                   506/9

(Continued)

FOREIGN PATENT DOCUMENTS

JP   2006-11415 A    1/2006
JP   2006-171227 A   6/2006
JP   2006-314214 A   11/2006

OTHER PUBLICATIONS

Japanese Notification of Reasons for Refusal, dated Jun. 20, 2017, for Japanese Application No. 2014-200942, with an English translation.

(Continued)

*Primary Examiner* — Idowu O Osifade
(74) *Attorney, Agent, or Firm* — Birch, Stewart, Kolasch & Birch, LLP

(57) ABSTRACT

A cell culture observation device and a cell culture observation method which observe a plurality of culture containers and perform operations for each culture container capture an image without blurring caused by the operations for the culture container and improve the throughput of processing for the plurality of culture containers. The cell culture observation device includes a cell observation unit 30 that observes cells in each of a plurality of culture containers in which the cells are cultured, an operating unit 20 that performs a plurality of operations for each of the culture containers, and an operation content determination unit 41 that determines the content of an operation which can be performed for culture containers other than a culture container to be observed while the culture container to be observed is being observed among the plurality of operations.

20 Claims, 6 Drawing Sheets

(56) References Cited

U.S. PATENT DOCUMENTS

2014/0363838 A1* 12/2014 McDevitt .......... G01N 33/5005
　　　　　　　　　　　　　　　　　　　　　　　　435/29
2015/0050687 A1　　2/2015 Arai

OTHER PUBLICATIONS

Extended European Search Report, dated Sep. 15, 2017, for European Application No. 15847723.2.
English Translation of the International Preliminary Report on Patentability and Written Opinion dated Apr. 4, 2017 in PCT/JP2015/076554.
International Search Report, issued in PCT/JP2015/076554, PCT/ISA/210, dated Dec. 28, 2015.
Written Opinion of the International Searching Authority, issued in PCT/JP2015/076554, PCT/ISA/237, dated Dec. 28, 2015.

* cited by examiner

FIG. 2

| MAGNIFICATION(P) | P≤4 | P≥20 | 4<P<20 |
|---|---|---|---|
| SCORE | 0 | 3 | 1 |
| EXPOSURE TIME(T) | T≤10ms | T≥250ms | 10ms<T<250ms |
| SCORE | 0 | 2 | 1 |
| OBSERVATION METHOD | BRIGHT FIELD OBSERVATION | PHASE DIFFERENCE OBSERVATION AND DIFFERENTIAL INTERFERENCE OBSERVATION | FLUORESCENT OBSERVATION |
| SCORE | 0 | 2 | 1 |
| IMAGING INTERVAL(TI) | TI≥40 MINUTES | TI≤20 MINUTES | 20 MINUTES<TI<40 MINUTES |
| SCORE | 0 | 2 | 1 |
| NUMBER OF IMAGING OPERATION(N) | N≥5 | N=1 | 2≤N≤4 |
| SCORE | 0 | 2 | 1 |

FIG. 5

| TYPE OF CELL | iPS CELL<br>ES CELL | MESENCHYMAL STEM CELL | CELLS OTHER THAN CELLS DESCRIBED ON LEFT SIDE |
|---|---|---|---|
| SCORE | 2 | 1 | 0 |
| TYPE OF CULTURE MEDIUM | CULTURE MEDIUM A | CULTURE MEDIUM B | CULTURE MEDIUM C |
| SCORE | 1 | 2 | 0 |
| TYPE OF SCAFFOLD | SCAFFOLD A | SCAFFOLD B | SCAFFOLD C |
| SCORE | 1 | 2 | 0 |
| CULTURE METHOD | PLANE CULTURE | | FLOATING CULTURE |
| SCORE | 0 | | 4 |

…

CELL CULTURE OBSERVATION DEVICE AND METHOD TO DETERMINE A CONTENT OPERATION

CROSS-REFERENCE TO RELATED APPLICATIONS

This application is a Continuation of PCT International Application No. PCT/JP2015/076554 filed on Sep. 17, 2015, which claims priority under 35 U.S.C § 119(a) to Japanese Patent Application No. 2014-200942 filed on Sep. 30, 2014. Each of the above application(s) is hereby expressly incorporated by reference, in its entirety, into the present application.

BACKGROUND OF THE INVENTION

1. Field of the Invention

The present invention relates to a cell culture observation device and a cell culture observation method which observe a plurality of culture containers and perform operations for each culture container.

2. Description of the Related Art

In recent years, an automatic culture observation device for culturing a large number of cells has been developed. The automatic culture observation device is configured so as to automatically perform various operations, such as a culture medium exchange operation, a chemical addition operation, and an operation of detaching and removing cells from a culture container, and to automatically observe cells in the culture container.

In general, in the automatic culture observation device, a cell operation unit that performs operations for cells and a cell observation unit that observes cells in the culture container are separated from each other. However, with a reduction in the size of the automatic culture observation device, a structure has been proposed in which the cell operating unit and the cell observation unit are integrated with each other.

However, in the integrated automatic culture observation device, in some cases, when an operation is performed for a predetermined culture container during the observation of cells in the culture container, a captured image is blurred and a clear image is not obtained.

For this reason, for example, JP2006-11415A discloses a technique that restricts the capture of the image of cells while culture media are exchanged. In addition, JP2006-314214A discloses a technique which temporarily stops the circulation of a culture fluid in synchronization with an imaging time to prevent the blurring of an image in floating culture.

SUMMARY OF THE INVENTION

However, JP2006-11415A and JP2006-314214A disclose a technique which restricts the capture of the image of the cell to be operated or restricts an operation for the cell to be observed, that is, a technique in which the observation of a predetermined culture container and the operation for the predetermined culture container are not performed at the same time, but does not consider an influence on the image, for example, when operations are performed for culture containers other than the culture container to be observed while the culture container to be observed is being observed.

In a case in which the device in which the cell operating unit and the cell observation unit are integrated with each other is considered, since a position where an operation is performed for cells is relatively close to a position where cells are observed, operations for culture containers other than the culture container to be observed are likely to affect the capture of the image of the culture container to be observed.

As disclosed in JP2006-11415A and JP2006-314214A, in a simple method which stops an operation while cells in a predetermined culture container are observed, in a case in which there are a large number of culture containers, it is difficult to perform operations for all of the culture containers other than the predetermined culture container while the predetermined culture container is being observed, which causes low throughput.

The invention has been made in view of the above-mentioned problems and an object of the invention is to provide a cell culture observation device and a cell culture observation method which can capture an image without blurring caused by an operation for a culture container and can improve the throughput of processing for a plurality of culture containers.

A cell culture observation device according to the invention comprises: a cell observation unit that observes cells in each of a plurality of culture containers in which the cells are cultured; an operating unit that performs a plurality of operations for each of the culture containers; and an operation content determination unit that determines a content of operation which can be performed for culture containers other than a culture container to be observed while the culture container to be observed is being observed among the plurality of operations.

The operation content determination unit may determine the content of operation which can be performed on the basis of observation conditions of the culture container to be observed.

Preferably the observation conditions include at least one of an exposure time of an imaging element that captures an image of the cells, a magnification of an optical system that observes the cells, an imaging interval of the cells, a number of imaging operation of the cells, or an observation method of the cells.

Preferably, the observation method includes at least one of bright field observation, phase difference observation, differential interference observation, or fluorescent observation.

The operation content determination unit may determine the content of operation which can be performed further on the basis of a type of the cells.

The operation content determination unit may determine the content of operation which can be performed further on the basis of culture conditions of the cells.

Preferably, the culture conditions include at least one of plane culture, floating culture, three-dimensional culture, a type of scaffold, a type of culture medium, or a type of chemical added to a culture medium.

The operation content determination unit may calculate a determination value on the basis of the observation conditions and determine the content of operation which can be performed on the basis of the determination value.

Preferably, the content of operation includes at least one of a culture medium exchange operation, an operation of adding the chemical to the culture medium, a culture container transport operation, a cell subculturing operation, or a cell detachment operation.

The cell culture observation device may further comprise a transport unit that transports the culture container between a culture unit that cultures the cells and the cell observation unit.

The cell culture observation device may further comprise a display control unit that displays the content of operation which can be performed.

The cell culture observation device may further comprise a control unit that determines an observation time of the culture container to be observed and an operation time of culture containers other than the culture container to be observed, on the basis of the content of operation determined by the operation content determination unit.

A cell culture observation method according to the invention observes cells in each of a plurality of culture containers in which the cells are cultured and performs a plurality of operations for each of the culture containers. The cell culture observation method comprises determining a content of operation which can be performed for culture containers other than a culture container to be observed while the culture container to be observed is being observed among the plurality of operations.

According to the cell culture observation device and the cell culture observation method of the invention, when cells in each of a plurality of culture containers are observed and a plurality of operations are performed for each culture container, the content of an operation which can be performed for culture containers other than the culture container to be observed while the culture container to be observed is being observed is determined among the plurality of operations. Therefore, even while cells in the culture container to be observed are being observed, an operation which does not affect the image to be observed can be determined and performed for other culture containers. As a result, it is possible to capture an image without blurring caused by the operation for the culture container and to improve the throughput of processing for a plurality of culture containers.

BRIEF DESCRIPTION OF THE DRAWINGS

FIG. 2 is a diagram illustrating an example of a table in which various observation conditions are associated with scores.

FIG. 5 is a diagram illustrating an example of a table in which the type of cell and culture conditions (the type of culture medium, the type of scaffold, and a culture method) are associated with scores.

DESCRIPTION OF THE PREFERRED EMBODIMENTS

Figure 1:
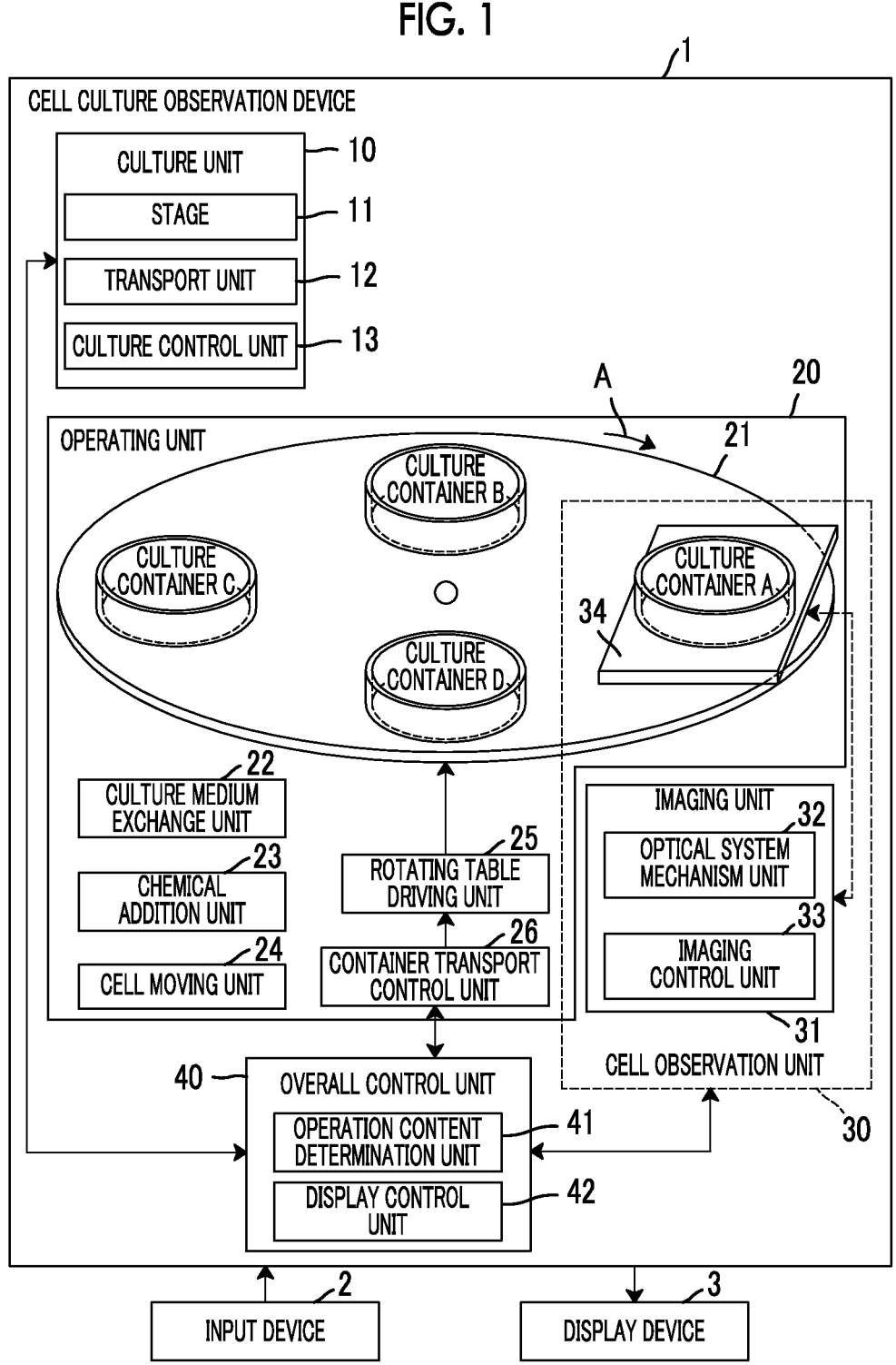
FIG. 1 is a block diagram schematically illustrating the structure of an embodiment of a cell culture observation device according to the invention.

Hereinafter, an embodiment of a cell culture observation device according to the invention will be described in detail with reference to the drawings. FIG. 1 is a block diagram schematically illustrating the structure of a cell culture observation device 1 according to this embodiment.

The cell culture observation device 1 according to this embodiment has a structure in which a culture unit that cultures cells, an operating unit that operates cells, and a cell observation unit that observes cells are integrated into one housing. Specifically, as illustrated in FIG. 1, the cell culture observation device 1 comprises a culture unit 10, an operating unit 20, a cell observation unit 30, and an overall control unit 40. The cell culture observation device 1 is connected to an input device 2 and a display device 3.

The culture unit 10 cultures cells. Examples of the cell to be cultured include pluripotent stem cells, such as iPS cells and ES cells, nerve cells, skin cells, heart cells, and liver cells which are differentiated and induced from the stem cells, and skin cells, retina cells, heart cells, blood cells, nerve cells, and organ cells which are extracted from the human body.

The culture unit 10 includes a plurality of culture containers in which the cells to be cultured are seeded in a culture medium. The culture unit 10 comprises a stage 11, a transport unit 12 and a culture control unit 13.

The culture container in which the cells to be cultured are seeded in a culture medium is placed on the stage 11. The stage 11 may comprise a mechanism for shaking the culture container.

The transport unit 12 transports the culture container placed on the stage 11 to a rotating table 21 in the operating unit 20 or transports the culture container placed on the rotating table 21 to the stage 11, for example, when a culture medium exchange operation, a chemical addition operation, or a cell detachment or subculturing operation is performed for the culture container or when the image of cells in the culture container is captured. For example, the transport unit 12 may have a structure in which it comprises a robot arm and holds the culture container with the robot arm and transports the culture container or a structure in which it comprises a transport belt and a driving mechanism for the transport belt and transports the culture container with the transport belt.

A culture control unit 13 controls the overall operation of the culture unit 10 and controls, for example, the operation of the transport unit 12 and culture conditions in the culture unit 10. Specifically, the culture control unit 13 controls culture conditions in the culture unit 10, such as temperature, humidity, the illuminance of a light source, oxygen concentration, carbon dioxide concentration, and the shaking conditions of the stage 11. A known structure can be used to adjust the culture conditions.

The operating unit 20 comprises the rotating table 21, a culture medium exchange unit 22, a chemical addition unit 23, a cell moving unit 24, a rotating table driving unit 25, and a container transport control unit 26.

As illustrated in FIG. 1, the rotating table 21 comprises a circular table and a plurality of culture containers A to D which are arranged on the circular table. The rotating table 21 is rotated in the direction of an arrow A by a rotating table driving mechanism. The culture containers are transported between the culture unit 10 and the cell observation unit 30 by the rotation. In this embodiment, the rotating table 21 corresponds to a transport unit according to the invention.

The rotating table driving unit 25 rotates the rotating table 21 on the basis of a control signal output from the container transport control unit 26. In addition, the container transport control unit 26 controls the driving of the rotating table driving unit 25 and rotates the rotating table 21 when the culture container is transported between the stage 11 of the culture unit 10 and the rotating table 21 or in a case in which the culture containers to be observed are switched in the cell observation unit 30.

The culture medium exchange unit 22 exchanges the culture media in the culture containers A to D placed on the rotating table 21. The culture medium exchange unit 22 may comprise, for example, a suction and supply mechanism that sucks the culture media in the culture containers A to D using pipette nozzles and discard the culture media or sucks a new culture medium using the pipette nozzles and supplies the culture medium into the culture container.

The chemical addition unit 23 adds chemicals to the culture containers A to D placed on the rotating table 21. An example of the chemical added by the chemical addition unit 23 is trypsin for detaching cells from the culture container. However, other chemicals may be used. The chemical addition unit 23 may comprise a suction and supply mechanism that sucks chemicals using pipette nozzles and supplies the chemicals into the culture container.

The cell moving unit 24 moves cells when cells are seeded in the culture container, when cells in the culture containers are detached, or when cells in the culture container are subcultured. The cell moving unit 24 may comprise, for example, a suction and supply mechanism that sucks cells using pipette nozzles, moves the cells to the culture container which is a seed destination or to the culture container in which the cells are subcultured, and supplies the cells into the culture container.

The culture medium exchange unit 22, the chemical addition unit 23, and the cell moving unit 24 may have a known structure.

The overall control unit 40 controls the operation of the culture medium exchange unit 22, the chemical addition unit 23, and the cell moving unit 24. When various operations including the culture medium exchange operation are performed for any one of a plurality of culture containers placed on the rotating table 21, the culture container to be operated is transported to a predetermined position by the rotating table 21 and the above-mentioned operation is performed at the predetermined position.

The cell observation unit 30 comprises an imaging unit 31 and a cell observation stage 34. The imaging unit 31 comprises an optical system mechanism unit 32 and an imaging control unit 33.

The optical system mechanism unit 32 is configured so as to switch bright field observation, phase difference observation, differential interference observation, and fluorescent observation and comprises a light source and an optical element used for each observation method. In addition, the optical system mechanism unit 32 comprises an imaging element, such as a complementary metal-oxide semiconductor (CMOS) sensor or a charge-coupled device (CCD) sensor. The imaging element outputs an image signal obtained by capturing the image of the cells in the culture container.

The imaging control unit 33 controls the overall operation of the imaging unit 31 and switches, for example, the light source or the optical element to be used to control switching between four observation methods. In addition, the imaging control unit 33 controls the magnification of an optical system of the optical system mechanism unit 32 or controls the operation of the imaging element. Specifically, the imaging control unit 33 controls the exposure time of the imaging element, the imaging interval of the imaging element, and the number of imaging operation of the imaging element.

The observation conditions, such as an optical magnification, an observation method, and the operation of the imaging element, are set and registered for each culture container in advance and are stored in the overall control unit 40 which will be described below. The imaging control unit 33 acquires the observation conditions for each culture container from the overall control unit 40 and controls the optical system mechanism unit 32 such that imaging is performed under the observation conditions corresponding to the culture container to be observed.

The culture container to be observed by the imaging unit 31 is placed on the cell observation stage 34. The culture container to be observed is transported from the rotating table 21 to the cell observation stage 34 by a predetermined transport mechanism (not illustrated) on the basis of a control signal output from the overall control unit 40. The cell observation stage 34 is provided in the vicinity of the rotating table 21. The culture container to be observed is transported to the vicinity of the cell observation stage 34 by the rotating table 21 and is then transported from the rotating table 21 to the cell observation stage 34.

The overall control unit 40 controls the overall operation of the cell culture observation device 1. In particular, the overall control unit 40 according to this embodiment controls an operation time, such as the exchange time of a culture medium in a predetermined culture container, or the capture time of the image of cells in the cell observation unit 30.

The overall control unit 40 comprises an operation content determination unit 41. The operation content determination unit 41 determines the content of an operation which can be performed for culture containers other than the culture container to be observed while the culture container to be observed is being observed. The content of operation which can be performed for culture containers other than the culture container to be observed is determined for the following reason: in a case in which an operation is performed for culture containers other than the culture container to be observed while the culture container to be observed is being observed as described above, the operation is likely to affect the captured image of cells.

Specifically, the operation content determination unit 41 according to this embodiment determines the content of operation which can be performed for culture containers other than the culture container to be observed, on the basis of the observation conditions of the culture container to be observed.

The reason why the content of operation which can be performed for other culture containers is determined on the basis of the observation conditions is that sensitivity to an image variation caused by the operation for other culture containers is changed depending on the observation conditions. The image variation occurs due to a change in the position of the culture container to be observed which is caused by the operation for other culture containers.

For example, as the optical magnification increases, sensitivity to the image variation caused by a change in the position which is caused by the operation for other culture containers increases. In addition, as the exposure time of the imaging element increases, sensitivity to the image variation caused by a change in the position increases. In the phase difference observation, sensitivity to the image variation caused by a change in the position is higher than that in the bright field observation. From this point of view, the operation content determination unit 41 according to this embodiment determines the content of operation for other culture containers on the basis of the observation conditions.

Specifically, a table in which various observation conditions are associated with scores as illustrated in FIG. 2 is set in the operation content determination unit 41 in advance. As described above, the observation conditions are set and registered for each culture container in the overall control unit 40 in advance. The operation content determination unit 41 acquires the observation conditions set for each culture container and acquires the scores on the basis of the observation conditions, with reference to the table illustrated in FIG. 2. Then, the operation content determination unit 41 determines the content of operation which can be performed for culture containers other than the culture container to be observed while the culture container to be observed is being observed, on the basis of the sum of the scores. In this embodiment, the score corresponds to a determination value according to the invention.

The scores in the table illustrated in FIG. 2 are set such that the observation condition with higher sensitivity to an image variation caused by a change in the position of the culture container to be observed has a higher score. For example, as the optical magnification increases, sensitivity to an image variation increases. Therefore, a higher score is given to a higher optical magnification. In addition, as the exposure time of the imaging element increases, sensitivity to an image variation increases. Therefore, a higher score is given to a longer exposure time.

For the observation method, the phase difference observation or the differential interference observation is diffracted light or interfering light observation. Therefore, in the phase difference observation or the differential interference observation, sensitivity to an image variation is higher than that in the fluorescent observation or the bright field observation. In the fluorescent observation, light intensity is lower than that in the bright field observation. Therefore, in the fluorescent observation, sensitivity to an image variation is higher than that in the bright field observation. Therefore, the highest score is given to the phase difference observation or the differential interference observation, the second highest score is given to the fluorescent observation, and the lowest score is given to the bright field observation.

The imaging interval means the interval between an N-th imaging operation and an (N+1)-th imaging operation in time lapse imaging. When the time interval is short, imaging needs to be performed while attention is paid to a change in an imaging target. Therefore, a higher score is given to a shorter imaging interval.

For the number of imaging operation, for example, as the number of imaging operation increases for a predetermined period of time, the exposure time is reduced. Therefore, similarly to the exposure time, as the number of imaging operation increases, sensitivity to an image variation is reduced. A lower score is given to a larger number of imaging operation. For example, in a case in which the number of imaging operation is 1 for a predetermined period of time, the score may be "2". In a case in which the number of imaging operation is 2 to 4, the score may be "1". In a case in which the number of imaging operation is equal to or greater than 5, the score may be "0". The number of imaging operation means the number of imaging operation for a predetermined period of time, as described above. For example, there is a case in which one imaging operation is performed with an exposure time of 100 ms or a case in which 10 imaging operations are repeatedly performed with an exposure time of 10 ms at an interval of 1 ns and the captured images are added.

Then, the operation content determination unit 41 calculates the sum of the scores on the basis of the observation conditions which are set for each culture container as described above and determines the content of operation which can be performed on the basis of the sum of the scores.

Specifically, for example, in a case in which the sum of the scores is equal to or less than 3, sensitivity to an image variation is low and all of the operations for other culture containers can be performed. In a case in which the sum of the scores is equal to or greater than 7, sensitivity to an image variation is high and all of the operations for other culture containers are not capable of being performed. In a case in which the sum of the scores is equal to or greater than 4 and equal to or less than 6, sensitivity to an image variation is medium. Therefore, the culture medium exchange operation, the chemical addition operation, and the operation of transporting the culture container using the rotating table 21 can be performed and the cell detachment operation and the subculturing operation in which a change in the position of the culture container to be observed or the culture container to be observed is likely to be large are not capable of being performed.

Next, a method for calculating the sum of the scores will be described, using a detailed example of the observation conditions of the culture container. For example, in a case in which the observation conditions of the culture container A are that the optical magnification is 4, the exposure time is 10 ms, the observation method is the phase difference observation, and the imaging interval is 15 minutes, the score of the optical magnification is "0", the score of the exposure time is "0", the score of the observation method is "2", and the score of the imaging interval is "2". Therefore, the sum of the scores is "4". In this case, the operation content determination unit 41 determines that the content of operation which can be performed for the culture containers B to D other than the culture container A while the culture container A is being observed is the culture medium exchange operation, the chemical addition operation, and the operation of transporting the culture container using the rotating table 21 and determines that the cell detachment operation and the subculturing operation are not capable of being performed.

For example, in a case in which the observation conditions of the culture container B are that the optical magnification is 40, the exposure time is 100 ms, the observation method is the phase difference observation, and the imaging interval is 15 minutes, the score of the optical magnification is "3", the score of the exposure time is "1", the score of the observation method is "2", and the score of the imaging interval is "2". Therefore, the sum of the scores is "8". In this case, the operation content determination unit 41 determines that all of the operations are not capable of being performed for the culture containers A, C, and D other than the culture container B while the culture container B is being observed.

For example, in a case in which the observation conditions of the culture container C are that the optical magnification is 10, the exposure time is 10 ms, the observation method is the bright field observation, and the imaging interval is 15 minutes, the score of the optical magnification is "1", the score of the exposure time is "0", the score of the observation method is "0", and the score of the imaging interval is "2". Therefore, the sum of the scores is "3". In this case, the operation content determination unit 41 determines that all of the operations can be performed for the culture containers A, B, and D other than the culture container C while the culture container C is being observed.

Then, the overall control unit 40 controls the observation time of the culture container to be observed and the operation time of culture containers other than the culture container to be observed, on the basis of the content determined by the operation content determination unit 41. That is, when a predetermined culture container to be observed is observed, the overall control unit 40 performs control such that only the feasible operations determined on the basis of the observation conditions are performed for the other culture containers and the operations which have been determined to be infeasible are performed at the time other than the observation time. A detailed example of the control of the observation time and the operation time will be described in detail below. In this embodiment, the overall control unit 40 corresponds to a control unit according to the invention.

Returning to FIG. 1, the overall control unit 40 comprises a display control unit 42. The display control unit 42 displays, for example, the image of the cell captured by the imaging unit 31 of the cell observation unit 30, the content of operation which can be performed determined by the operation content determination unit 41, and the observation conditions for each culture container on the display device 3. The display device 3 is, for example, a display such as a liquid crystal display.

The input device 2 comprises, for example, a mouse and a keyboard and receives settings input by the user. The input device 2 according to this embodiment receives the setting and change of the observation conditions for each culture container or receives the setting and change of the scores in the table illustrated in FIG. 2. The display device 3 may also function as the input device. In this case, the display device 3 includes a touch panel screen and the user presses the screen to input settings.

Figure 3:
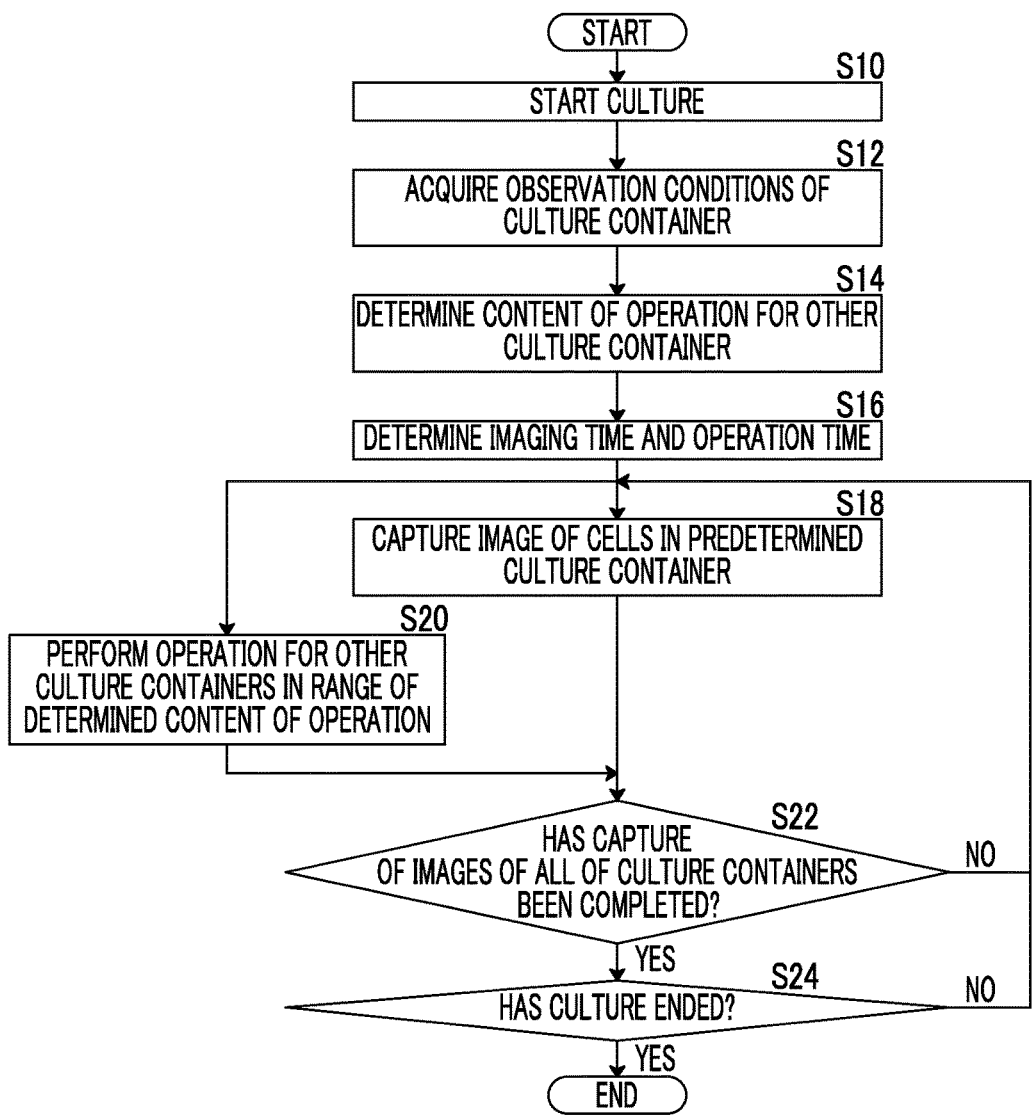
FIG. 3 is a flowchart illustrating the operation of the embodiment of the cell culture observation device according to the invention.

Next, the operation of the cell culture observation device 1 according to this embodiment will be described with reference to the flowchart illustrated in FIG. 3.

First, a plurality of culture containers in which the cells to be cultured are seeded are placed on the stage 11 of the culture unit 10 and culture starts (S10).

Then, for example, when an operation of capturing the image of the cells in each culture container and exchanging the culture media in each culture container is performed after a predetermined culture period has elapsed, for example, the operation content determination unit 41 acquires the observation conditions for each culture container in response to an instruction which is input by the user through the input device 2 (S12). In addition, the observation conditions for each culture container are set and registered in the overall control unit 40 by the user in advance, as described above.

The operation content determination unit 41 determines the content of an operation which can be performed for culture containers other than the culture container to be observed while the culture container to be observed is being observed, among the operations for each culture container, on the basis of the acquired observation conditions for each culture container (S14). That is, when a predetermined culture container is observed, the operation content determination unit 41 determines the content of operation which can be performed for other culture containers.

Then, the overall control unit 40 determines the observation time of the culture container to be observed and the operation time of the culture containers other than the culture container to be observed, on the basis of the content of operation which can be performed determined by the operation content determination unit 41 (S16). That is, the overall control unit 40 determines the observation time and the operation time of each culture container such that only the content of operation determined to be feasible is performed for other culture containers while the culture container to be observed is being observed. A detailed example of the observation time and the operation time of each culture container will be described in detail below.

Then, the overall control unit 40 outputs a control signal to the cell observation unit 30 on the basis of the determined observation time of each culture container and the cell observation unit 30 captures the image of cells in the culture container to be observed, on the basis of the input control signal (S18). The overall control unit 40 outputs a control signal to the operating unit 20 on the basis of the determined operation time of each culture container and the operating unit 20 performs an operation for each culture container on the basis of the input control signal (S20).

Specifically, the rotating table driving unit 25 rotates the rotating table 21 on the basis of the control signals from the overall control unit 40 and the container transport control unit 26. The rotating table 21 is rotated according to the observation time of each culture container and the culture containers on the rotating table 21 are sequentially transported to the cell observation stage 34. The image of cells in each culture container is sequentially captured.

The operating unit 20 performs the operation of transporting the culture container using the rotating table 21, the culture medium exchange operation, the chemical addition operation, or the cell moving operation (the cell detachment operation or the subculturing operation) for the culture containers other than the culture container to be observed, on the basis of the control signal from the overall control unit 40. At that time, only the content of operation determined to be feasible by the operation content determination unit 41 is performed.

When the capture of the image of the culture container to be observed and the operation for the culture containers other than the culture container to be observed are performed and the capture of the images of all of the culture containers set as the observation target is completed in this way, a series of imaging processes and operations ends (YES in S22).

Then, the capture of the image of cells in the culture container and the process for the culture container are repeatedly performed at a predetermined interval or an interval that is set by the user in advance. Then, when the culture of the cells in the culture container is completed, the process ends (YES in S24).

Figure 4:
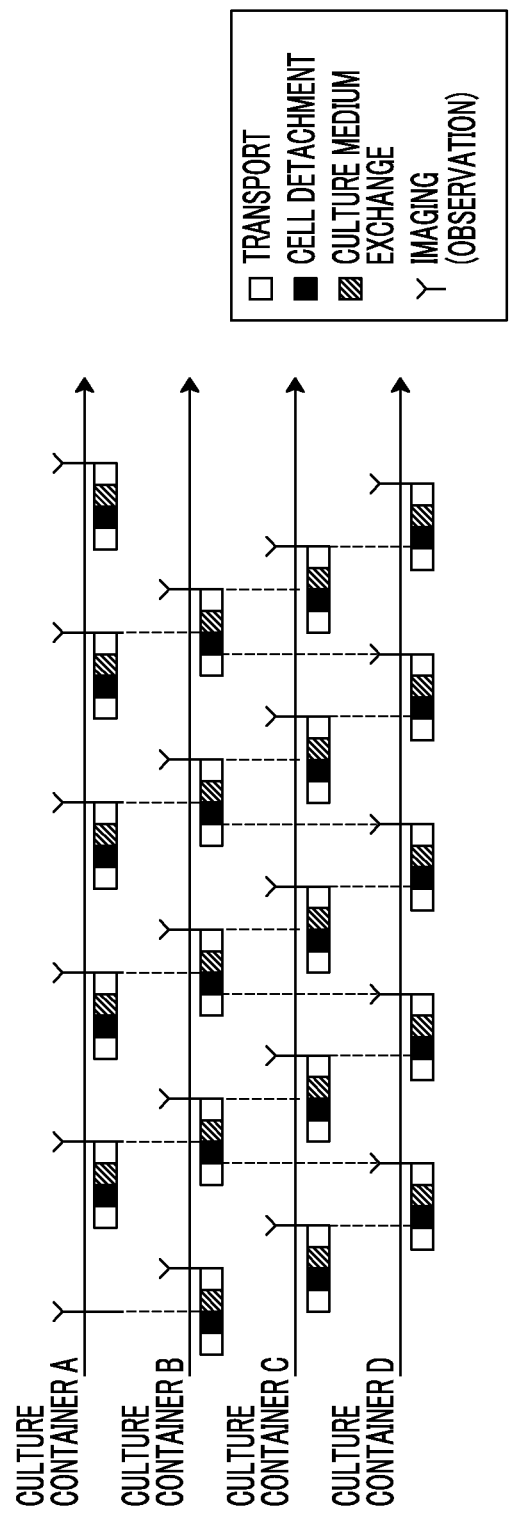
FIG. 4 is a timing chart illustrating the observation time and the operation time of culture containers A to D.

Here, a detailed example of the observation time and the operation time of each culture container in the cell culture observation device 1 according to this embodiment will be described. FIG. 4 is a timing chart illustrating the observation time and the operation time of four culture containers A to D. This example shows a timing chart when the operation of capturing the image (observing) of cells in the culture container, the operation of transporting the culture container, of which the image has been captured, using the rotating table 21, the cell detachment operation, the culture medium exchange operation, and the operation of transporting the culture container, of which the culture medium has been exchanged, using the rotating table 21 are repeatedly performed for each culture container in this order.

This example corresponds to a case in which the operation content determination unit 41 determines the content of operation which can be performed on the basis of the observation conditions of each of the culture containers A to D and it is determined that operations other than the cell detachment operation can be performed for all of the culture containers A to D while the culture container to be observed is being observed.

Figure 6:
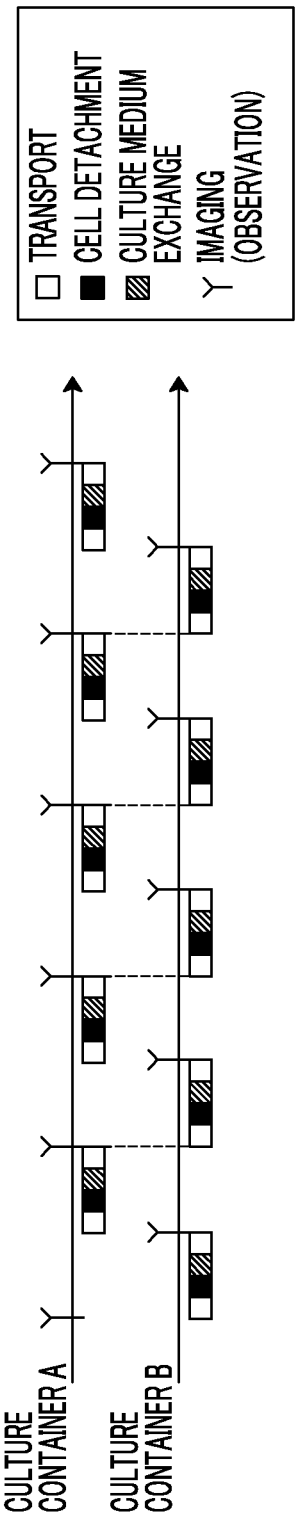
FIG. 6 is a timing chart illustrating the observation time and the operation time of each culture container in a case in which, while a culture container to be observed is observed, all operations are not performed for other culture containers.

As illustrated in FIG. 4, the imaging (observation) time of each of the culture containers A to D is controlled such that it does not overlap the time of the cell detachment operation for each culture container. This control makes it possible to perform the culture medium exchange operation and the culture container transport operation other than the cell detachment operation for other culture containers even while a predetermined culture container is being observed. Therefore, it is possible to process a large number of culture containers in a short time. FIG. 6 is a timing chart illustrating the observation time and the operation time of each culture container in a case in which, while the culture container to be observed is being observed, all of the operations are not performed for other culture containers. In this case, as can be seen from FIG. 6, throughput is lower than that in the timing chart illustrated in FIG. 4.

In the above-described embodiment, a case in which all of the culture containers A to D are sequentially set as an observation target and the images thereof are captured has been described. However, the invention is not limited to the case. For example, the invention can be applied to a case in which a predetermined culture container is selected from a plurality of culture containers and is set as the observation target and the image thereof is captured. In this case, operations which can be performed for culture containers other than the culture container selected as the observation target are determined on the basis of the observation conditions of the culture container to be observed.

In the cell culture observation device 1 according to the embodiment described above, scores are acquired on the basis of the observation conditions, such as optical magnification or the like, and the content of an operation for the culture container is determined on the basis of the sum of the scores. However, the invention is not limited thereto. For example, scores may be acquired on the basis of the type of cell and the culture conditions and the sum of scores including the scores may be calculated.

FIG. 5 is a diagram illustrating an example of a table in which the type of cell and the culture conditions (the type of culture medium, the type of scaffold, and a culture method) are associated with scores. Specifically, for example, for the type of cell, the adhesion of cells to the culture container varies depending on the type of cell. Therefore, sensitivity to an image variation caused by a change in the position of the culture container varies depending on the type of cell. For example, the adhesion of an iPS cell and an ES cell to the culture container is relatively low and the adhesion of a mesenchymal stem cell to the culture container is relatively high. Therefore, in a case in which the type of cell is an iPS cell and an ES cell, the score is set to "2". In a case in which the type of cell is a mesenchymal stem cell, the score is set to "1". In a case in which the type of cell is cells other than the iPS cell, the ES cell, and the mesenchymal stem cell, the score is set to "0". In addition, for the type of scaffold, the adhesion of cells varies depending on the type of scaffold. Therefore, the score is set according to the type of scaffold.

For the type of culture medium, the ease of the movement of cells varies depending on, for example, the viscosity of a culture medium. Therefore, sensitivity to an image variation caused by a change in the position of the culture container varies depending on the type of culture medium. Different scores are set according to the type of culture medium. For the culture method, the ease of the movement of cells varies depending on, for example, the culture method. Therefore, sensitivity to an image variation caused by a change in the position of the culture container varies depending on the culture method. Specifically, cells are less likely to move in the case of plane culture and are likely to move in the case of floating culture. Therefore, in the case of plane culture, the score is set to "0". In the case of floating culture, the score is set to "4". In the table illustrated in FIG. 5, scores are shown in a case in which the culture method is plane culture and floating culture. The table may include the score of three-dimensional culture. In the case of three-dimensional culture, since cells are attached to a scaffold, the cells are less likely to be moved than those in floating culture. When the cells are piled up, it is considered that the cells have a higher susceptibility to variation than those in plane culture. Therefore, for example, the score is preferably set to "1".

As one of the culture conditions, the score may be set according to the type of chemical added to the culture medium. For example, in a case in which chemicals for promoting multiplication and growth are added, for example, the score is set to "0" since it is considered that the adhesion of cells to the scaffold is sufficient. In a case in which chemicals for promoting the detachment of cells from the scaffold are added, since this is similar to the case in which cells are detached from the scaffold and are cultured by the floating culture method, the score is set to "4".

The user sets and inputs information about the type of cell and the culture condition, using the input device 2. In addition, the user may additionally register the type of cell, the culture conditions, and scores corresponding to the type of cell and the culture conditions in the table.

The cell culture observation device 1 according to the embodiment controls the observation time and the operation time of each culture container on the basis of the determination result of the operation content determination unit 41. However, the invention is not limited thereto. For example, when the culture medium exchange operation, the chemical addition operation, the cell detachment operation, or the subculturing operation is manually performed, the content of operation which have been determined to be feasible by the operation content determination unit 41 may be displayed on the display device 3 such that the user who sees the displayed operations does not perform operations other than the operation which has been determined to be feasible for the culture containers other than a predetermined culture container while observing the predetermined culture container.

In the above-described embodiment, while the culture container which is an observation target is being observed, the content of operations for the culture containers other than the observation target is limited. In other words, while the operation which is not capable of being performed for the culture containers other than the observation target is being performed, the observation of the culture container which is the observation target is prohibited.

EXPLANATION OF REFERENCES

1: cell culture observation device
2: input device
3: display device
10: culture unit
11: stage
12: transport unit
13: culture control unit
20: operating unit
21: rotating table 22: culture medium exchange unit
23: chemical addition unit
24: cell moving unit
25: rotating table driving unit
26: container transport control unit
30: cell observation unit
31: imaging unit
32: optical system mechanism unit
33: imaging control unit
34: cell observation stage
40: overall control unit
41: operation content determination unit
42: display control unit

What is claimed is:

1. A cell culture observation device comprising:
a controller configured to:
observe cells in each of a plurality of culture containers in which the cells are cultured;
perform a plurality of operations for each of the culture containers; and
determine a content of operation which can be performed for culture containers other than a culture container to be observed while the culture container to be observed is being observed among the plurality of operations,
wherein the content of operation determined as being performable by the controller is performed by the controller during imaging of the culture container to be observed.

2. The cell culture observation device according to claim 1,
wherein the controller determines the content of operation which can be performed on the basis of observation conditions of the culture container to be observed.

3. The cell culture observation device according to claim 2,
wherein the observation conditions include at least one of an exposure time of an imaging element that captures an image of the cells, a magnification of an optical system that observes the cells, an imaging interval of the cells, a number of imaging operation of the cells, or an observation method of the cells.

4. The cell culture observation device according to claim 3,
wherein the observation method includes at least one of bright field observation, phase difference observation, differential interference observation, or fluorescent observation.

5. The cell culture observation device according to claim 2,
wherein the controller determines the content of operation which can be performed further on the basis of a type of the cells.

6. The cell culture observation device according to claim 3,
wherein the controller determines the content of operation which can be performed further on the basis of a type of the cells.

7. The cell culture observation device according to claim 4,
wherein the controller determines the content of operation which can be performed further on the basis of a type of the cells.

8. The cell culture observation device according to claim 2,
wherein the controller determines the content of operation which can be performed further on the basis of culture conditions of the cells.

9. The cell culture observation device according to claim 3,
wherein the controller determines the content of operation which can be performed further on the basis of culture conditions of the cells.

10. The cell culture observation device according to claim 4,
wherein the controller determines the content of operation which can be performed further on the basis of culture conditions of the cells.

11. The cell culture observation device according to claim 5,
wherein the controller determines the content of operation which can be performed further on the basis of culture conditions of the cells.

12. The cell culture observation device according to claim 6,
wherein the controller determines the content of operation which can be performed further on the basis of culture conditions of the cells.

13. The cell culture observation device according to claim 7,
wherein the controller determines the content of operation which can be performed further on the basis of culture conditions of the cells.

14. The cell culture observation device according to claim 8,
wherein the culture conditions include at least one of plane culture, floating culture, three-dimensional culture, a type of scaffold, a type of culture medium, or a type of chemical added to a culture medium.

15. The cell culture observation device according to claim 2,
wherein the controller calculates a determination value on the basis of the observation conditions and determines the content of operation which can be performed on the basis of the determination value.

16. The cell culture observation device according to claim 1,
wherein the content of operation includes at least one of a culture medium exchange operation, an operation of adding the chemical to the culture medium, a culture container transport operation, a cell subculturing operation, or a cell detachment operation.

17. The cell culture observation device according to claim 1, further comprising:
a transporter that transports the culture container.

18. The cell culture observation device according to claim 1, further comprising:
a display controller that displays the content of operation which can be performed.

19. The cell culture observation device according to claim 1, further comprising:
a controller that determines an observation time of the culture container to be observed and an operation time of culture containers other than the culture container to be observed, on the basis of the content of operation determined by the controller.

20. A cell culture observation method that observes cells in each of a plurality of culture containers in which the cells are cultured and performs a plurality of operations for each of the culture containers, using the cell culture observation device according to claim 1, the method comprising:
determining a content of operation which can be performed for culture containers other than a culture container to be observed while the culture container to be observed is being observed among the plurality of operations, wherein the content of operation determined as being performable is performed during imaging of the culture container to be observed.

* * * * *